US010041122B2

(12) United States Patent
Jaisser et al.

(10) Patent No.: US 10,041,122 B2
(45) **Date of Patent: *Aug. 7, 2018**

(54) BIOMARKERS OF MINERALOCORTICOID RECEPTOR ACTIVATION

(71) Applicant: INSERM (Institut National de la Sante et de la Recherche Medicale), Paris (FR)

(72) Inventors: Frederic Jaisser, Paris (FR); Nicolette Farman, Paris (FR); Yannis Sainte-Marie, Toulouse (FR); Celine Latouche, Melbourne VIC (AU); Marja Steenman, Nantes (FR)

(73) Assignee: INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/188,198

(22) Filed: Jun. 21, 2016

(65) Prior Publication Data

US 2016/0362744 A1 Dec. 15, 2016

Related U.S. Application Data

(63) Continuation of application No. 13/124,575, filed as application No. PCT/EP2009/063832 on Oct. 21, 2009.

(60) Provisional application No. 61/181,821, filed on May 28, 2009.

(30) Foreign Application Priority Data

Oct. 24, 2008 (EP) .................................... 08305728

(51) Int. Cl.

| | |
|---|---|
| ***C12Q 1/68*** | (2018.01) |
| ***G01N 33/68*** | (2006.01) |
| ***C12Q 1/6883*** | (2018.01) |

(52) U.S. Cl.

CPC ....... *C12Q 1/6883* (2013.01); *G01N 33/6893* (2013.01); *C12Q 2600/106* (2013.01); *C12Q 2600/158* (2013.01); *G01N 2800/04* (2013.01); *G01N 2800/042* (2013.01); *G01N 2800/044* (2013.01); *G01N 2800/32* (2013.01); *G01N 2800/321* (2013.01); *G01N 2800/325* (2013.01); *G01N 2800/52* (2013.01)

(58) Field of Classification Search

None

See application file for complete search history.

(56) References Cited

U.S. PATENT DOCUMENTS

| | | | | |
|---|---|---|---|---|
| 9,212,361 | B2 * | 12/2015 | Jaisser | C12N 15/113 |
| 9,533,041 | B2 * | 1/2017 | Jaisser | A61K 31/7105 |
| 9,594,083 | B2 * | 3/2017 | Jaisser | A61K 31/7088 |

FOREIGN PATENT DOCUMENTS

| | | |
|---|---|---|
| WO | 02/09683 | 2/2002 |
| WO | 2005/005601 | 1/2005 |
| WO | 2008/030370 | 3/2008 |
| WO | 2008/060607 | 5/2008 |

OTHER PUBLICATIONS

Bettencourt et al., Circulation, 110(15)2168-2174 (2004).
Boccanelli et al., J. Cardiovascular Medicine, 8(9):683-691 (2007).
Bolten et al., Endocrinology, 147(7)3181-3182 (2006).
Bradstreet et al., Medical Hypotheses, 68(5):979-987 (2007).
Cichy et al., FEBS Lett., 359(2-3):262-266 (1995).
Dik et al., Diabetes Care, 30(10):2655-2660 (2007).
Hak et al., J. Clin. Endocrin. Metabolism, 86(9):4398-4405 (2001).
Hansen et al., Immunol. Lett., 91(2-3):87-91 (2004).
Lim et al., Br. J. Clin. Pharmacol., 48(5):756-760 (1999).
Nagareda et al., J. Pathol., 165(4):319-324 (1991).
Owen et al., Am. J. Physiol. Endocrin. and Metabol., 294(6):E1023-E1034 (2008).
Palacios et al., Maturitas, 55(4):297-307 (2006).
Parthasarathy et al., BMC Cardiovascular Disorders, 7(1):14 (2007).
Parthasarathy et al., Br. J. Diabetes and Vascular Dis., 8(5):215-219 (2008).
Tsutamoto et al., J. Am. College of Caridol., 37(5):1228-1233 (2001).
Wang et al., Clin. Chem., Am. Assoc. Clin. Chem., 53(1):34-41 (2007).
Yan et al. (Diabetes 56: 2533-2540, 2007).
Zou, Qian-Ting, An Zhen-Mei, Adverse Impact of Aldosterone on Cardiovascular System and its Theray, West China Medical Journal 2007, vol. 22, No. 3, pp. 5/8 and 6/8.

* cited by examiner

*Primary Examiner* — Kortney L. Klinkel
*Assistant Examiner* — William Y Lee
(74) *Attorney, Agent, or Firm* — W&C IP

(57) ABSTRACT

The present invention relates to the use of Neutrophil Gelatinase-Associated Lipocalin (NGAL) and/or SERPINA3 as biomarkers of the Mineralocorticoid Receptor (MR) activation in a patient. More particularly, the present invention relates to a method for predicting the responsiveness of a patient to a treatment with a MR antagonist or an aldosterone synthase inhibitor, said method comprising determining in a biological sample obtained from said patient the expression level of the NGAL gene and/or of the SERPINA3 gene.

2 Claims, 10 Drawing Sheets

Figure 1A:
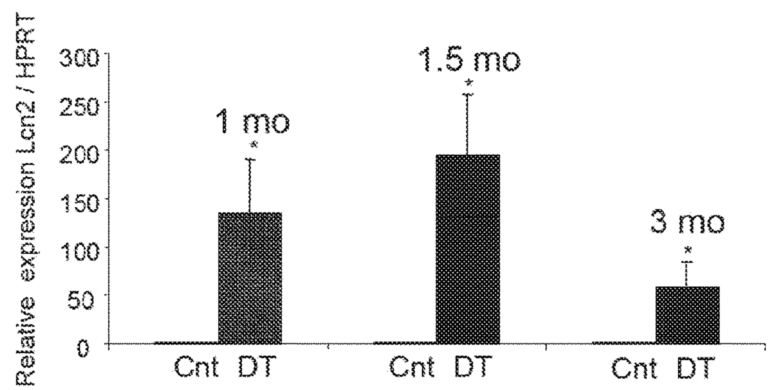

Fig. 3A
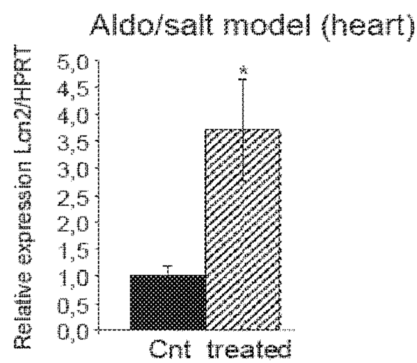
Fig. 3B
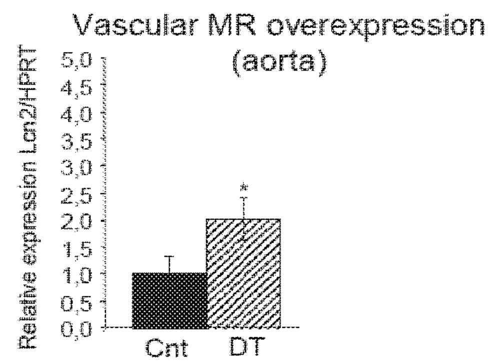
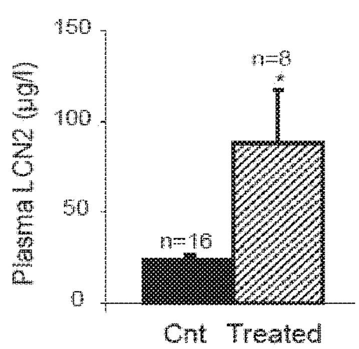
Fig. 3C
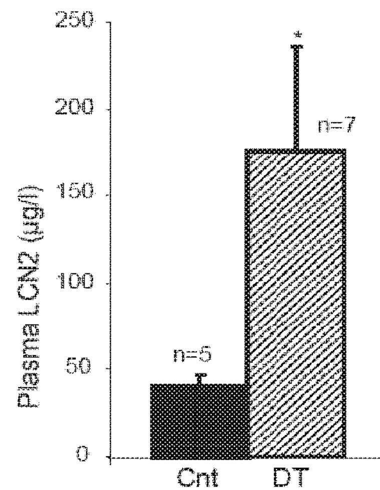
Fig. 3D

* p<0.05 vs sham, ** p<0.01 vs sham, # p<0.05 vs placebo , t-test.

BIOMARKERS OF MINERALOCORTICOID RECEPTOR ACTIVATION

This application is a continuation application of U.S. application Ser. No. 13/124,575, which was filed Jul. 7, 2011, and which is a National Stage Entry of International Application No. PCT/EP2009/063832, which was filed Oct. 21, 2009 and claims the benefit of priority to European Patent Application No. 08305728.1, which was filed on Oct. 24, 2008, and the benefit of priority to U.S. Provisional Application No. 61/181,821, which was filed on May 28, 2009. The entire text of the aforementioned applications is incorporated herein by reference in its entirety.

FIELD OF THE INVENTION

The present invention relates to biomarkers of the Mineralocorticoid Receptor (MR) activation in a patient.

BACKGROUND OF THE INVENTION

Mineralocorticoid receptor (MR) is a member of the classic steroid hormone receptors that include glucocorticoid receptor (GR), androgen receptor (AR), progesterone receptor (PR), and estrogen receptor (ER) (Funder, 1997). These receptors are hormone-activated transcriptional factors that regulate a wide variety of physiological processes ranging from organ development and differentiation to mood control and stress response (Beato et al., 1995). The physiological hormone for MR is aldosterone which is a steroid hormone secreted by the adrenal gland.

MRs have been located on non-epithelial sites in blood vessels, brain, and heart (Bonvalet J P. et al. 1995; Lombes M, et al. 1992; Tanaka J. et al. 1997). Numerous studies over the past 10 years suggest that the non-epithelial actions of mineralocorticoids are responsible for their vascular and myocardial fibrotic and trophic effects (Brilla C G. et al. 1992, Ullian M E. et al. 1992; Young M. et al. 1994) In addition, MRs have been discovered, including human endothelial cells and vascular smooth muscle cells (VSMC) (Hatakeyama H. et al. 1994) and myocardial cells in animal studies (Silvestre J S. et al. 1988). Several studies (Brilla C G et al. 1992; Young M. et al. 1994) have linked mineralocorticoids with myocardial fibrosis through stimulation of collagen formation in myocardial cells.

Farquharson C A. et al. (2000) indirectly showed that aldosterone could have a role in endothelial dysfunction in chronic heart failure. Therefore MR is an important drug target particularly for the treatment of hypertension and heart failure.

For example, the aldosterone antagonist spironolactone (also known as ALDACTONE®, PFIZER) binds to the mineralocorticoid receptor and blocks the binding of aldosterone. This steroidal compound is used commonly in the treatment of congestive heart failure. Actually, spironolactone has been shown to be pharmacologically effective and well tolerated, to reduce the overall risks of death, death due to progressive heart failure, and sudden death from cardiac causes, as well as the risk of hospitalization for cardiac causes. The administration of spironolactone to severe heart failure patients was evaluated in the Randomized Aldactone Evaluation Study (RALES). RALES was a randomized, double-blinded, placebo-controlled trial that enrolled participants who had severe heart failure and a left ventricular ejection fraction of no more than 35% and who were receiving standard therapy, which typically included an angiotensin-converting enzyme inhibitor, a loop diuretic, and, in some cases, digoxin. The RALES subjects treated with spironolactone had a statistically significant reduction in mortality and incidence of hospitalization relative to placebo-treated subjects (Pitt B. et al. 1999).

Likewise, eplerenone exemplifies another blocker of aldosterone binding at the mineralocorticoid receptor. Its action is selective, in that eplerenone binds to recombinant human mineralocorticoid receptors in preference to binding to recombinant human glucocorticoid, progesterone and androgen receptors. The therapeutic benefits associated with administration of eplerenone have been demonstrated in multiple clinical trials. In one such study involving over 6,600 subjects [the Eplerenone Post-Acute Myocardial Infarction Heart Failure Efficacy and Survival Study (EPHESUS)], eplerenone was found to reduce significantly the risk of death attributable to cardiovascular causes and the risk of hospitalization for cardiovascular events (Pitt B. et al. 2003). A reduction in the rate of sudden death from cardiac causes was also observed.

However aldosterone is not the only endogenous hormone known for activating the MR. For example, endogenous glucocorticoids can also activate the MR. Actually, glucocorticoids have been shown to produce oxidative stress and vascular inflammation at the earliest stages of the development of cardiac fibrosis. Deleterious effects of MR activation in the cardiovascular system may thus occur even in the absence of hyperaldosteronism (Funder J W, 2006) and plasma levels of aldosterone do not provide indication on the MR activation in the cardiovascular system. Moreover, MR expression is increased in heart or vessels in heart failure, cardiac infarction or end-organ damage associated to high blood pressure (Nagata K, et al. 2006; Takeda M. et al., 2007).

Thus there is still an existing need in the art to develop an accurate and specific method for assessing the MR activation in the cardiovascular system.

Furthermore, administration of a MR antagonist in a patient may be accompanied with serious adverse side effects such as hyperkalemia. Actually, there have been several reports of serious hyperkalemia following the publication of the RALES study. In one such report, no less than 25 patient episodes of spironolactone-related hyperkalemia that had to be treated in the emergency room were described (Schepkens H. et al. 2001). Four of the 25 patients required cardiovascular resuscitation measures, and 2 of the 25 patients died. Several authors have estimated an incidence of clinically significant hyperkalemia of about 10% in patients receiving this MR antagonist.

Therefore, there is also an existing need in the art to develop an accurate and specific method for predicting the responsiveness of a patient affected with heart failure to a treatment with a MR antagonist, in order to prevent or limit the adverse side effects of such a treatment.

SUMMARY OF THE INVENTION

The present invention relates to a method for assessing the Mineralocorticoid Receptor (MR) activation in a patient comprising determining in a biological sample obtained from said patient the expression level of one or two biomarkers selected from the group consisting of the Neutrophil Gelatinase-Associated Lipocalin (NGAL) gene and the SERPINA3 gene.

The present invention also relates to a method for predicting the responsiveness of a patient to a treatment with a MR antagonist or an aldosterone synthase inhibitor, said method comprising determining in a biological sample obtained from said patient the expression level of one or two biomarkers selected from the group consisting of the Neutrophil Gelatinase-Associated Lipocalin (NGAL) gene and the SERPINA3 gene.

The invention also relates to the use of a MR antagonist or an aldosterone synthase inhibitor, for treating a patient affected with a cardiovascular disease, diabetes, obesity or metabolic syndrome, said patient being classified as responder by the method of the invention.

DETAILED DESCRIPTION OF THE INVENTION

Definitions

The term "MR" refers to the mineralocorticoid receptor. As used herein, the term "MR activation" refers to the activation of the mineralocorticoid receptor by mineralocorticoids (i.e. aldosterone) or glucocorticoids.

The term "MR antagonist" refers to a compound, natural or not, which has the capability to inhibit (partly or totally) the biological activation of the MR. A number of MR antagonists are known including spironolactone, epoxymexrenone and eplerenone. The scope of the present invention includes all those MR antagonists now known and those MR antagonists to be discovered in the future. The aldosterone antagonist may be a spironolactone-type compound (Spironolactone, active metabolites of spironolactone such as canrenone or salts thereof such as potassium canrenoate). The aldosterone antagonist may also be an epoxy-steroidal aldosterone antagonist. Another series of steroidal-type MR antagonists is exemplified by epoxy-containing spironolactone derivatives. For example, U.S. Pat. No. 4,559,332 describes spironolactone derivatives as MR antagonists. A further MR antagonist may be Drospirenone (DRSP), which is an analogue to Spironolactone.

The term "aldosterone synthase inhibitor" is intended to include compounds or agents that inhibit the aldosterone synthase enzyme, which convert corticosterone to aldosterone by hydroxylating corticosterone to form 18-OH-corticosterone and 18-OH-corticosterone to aldosterone. A number of aldosterone synthase inhibitors are well known in the art. The scope of the present invention includes all those aldosterone synthase inhibitors now known and those aldosterone synthase inhibitors to be discovered in the future. Said aldosterone synthase inhibitor may be steroidal or non-steroidal aldosterone synthase inhibitors. The aldosterone synthase inhibitor may be a non-steroidal or steroidal aromatase inhibitor. Non-steroidal aromatase inhibitors may include anastrozole and fadrozole (including the (+)-enantiomer thereof). An example of a steroidal aromatase inhibitor is exemestane. Another non-steroidal aldosterone synthase inhibitor is the (+)-enantiomer of the hydrochloride of fadrozole (U.S. Pat. Nos. 4,617,307 and 4,889,861) as also described in Fiebeler A. et al. (2005).

The term "Lipocalin 2" or "NGAL" has its general meaning in the art and refers to the Neutrophil Gelatinase-Associated Lipocalin as described in Schmidt-Ott K M. et al. (2007). NGAL can be from any source, but typically is a mammalian (e.g., human and non-human primate) NGAL, particularly a human NGAL. The term "NGAL gene" refers to any nucleotide sequence encoding the NGAL mRNA and protein, such as a genomic DNA sequence and any naturally occurring NGAL and variants and modified forms thereof. It can also encompass artificial sequences such as cDNA encoding the NGAL mRNA and protein. An exemplary human native NGAL nucleotide sequence is provided in GenBank database under accession number NM_005564. The term "NGAL mRNA" has its general meaning in the art and refers to the messenger RNA which is synthesized upon expression of the NGAL gene. The term "NGAL protein" refers to the amino acid sequence resulting from the expression of the NGAL gene, and any naturally occurring NGAL and variants and modified forms thereof. An exemplary human native NGAL amino acid sequence is provided in GenPept database under accession number NP_005555. The term "NGAL protein" as used herein also encompasses the heterodimeric complex formed by NGAL and the metalloproteinase MMP-9, also known as gelatinase B, 92 kDa type IV collagenase, 92 kDa gelatinase and type V collagenase (Kjeldsen et a., 1993).

The term "anti-NGAL antibody" refers to an antibody or a fragment thereof which recognizes NGAL.

The term "SERPINA3" gene has its general meaning in the art, it is also known as CT; AACT; GIG24; GIG25; MGC88254. The official full name of this gene is serpin peptidase inhibitor, clade A (alpha-1 antiproteinase, antitrypsin), member 3. SERPINA3 can be from any source, but typically is a mammalian (e.g., human and non-human primate) SERPINA3, particularly a human SERPINA3. The term "SERPINA3 gene" refers to any nucleotide sequence encoding the SERPINA3 mRNA and protein, such as a genomic DNA sequence and any naturally occurring SERPINA3 and variants and modified forms thereof. It can also encompass artificial sequences such as cDNA encoding the SERPINA3 mRNA and protein. The term "SERPINA3 mRNA" has its general meaning in the art and refers to the messenger RNA which is synthesized upon expression of the SERPINA3 gene. The term "SERPINA3 protein" refers to the amino acid sequence resulting from the expression of the SERPINA3 gene, and any naturally occurring SERPINA3 and variants and modified forms thereof.

The term "SERPINA3 antibody" refers to an antibody or a fragment thereof which recognizes the SERPINA3 protein.

The term "cardiovascular system" has its general meaning in the art, and denotes the system composed of the heart, blood vessels, or vasculature, and the cells and plasma that make up the blood.

The term "cardiovascular disease" has its general meaning in the art and is used to classify numerous conditions that affect the heart, heart valves, blood, and vasculature of the body. Cardiovascular diseases include endothelial dysfunction, coronary artery disease, angina pectoris, myocardial infarction, congestive heart failure, hypertension, cerebrovascular disease, stroke, transient ischemic attacks, deep vein thrombosis, peripheral artery disease, cardiomyopathy, arrhythmias, aortic stenosis, and aneurysm.

As used herein, the term "predetermined value of a biomarker" refers to the amount of the biomarker in biological samples obtained from the general population or from a selected population of subjects. For example, the selected population may be comprised of apparently healthy subjects, such as individuals who have not previously had any sign or symptoms indicating the presence of cardiovascular disease. In another example, the predetermined value may be of the amount of biomarker obtained from subjects having an established cardiovascular disease. The predetermined value can be a threshold value, or a range. The predetermined value can be established based upon comparative measurements between apparently healthy subjects and subjects with established cardiovascular disease.

The term "patient" as used herein denotes a mammal such as a rodent, a feline, a canine and a primate. Preferably, a patient according to the invention is a human.

A "responder" or "responsive" patient, or group of patients, to a treatment with a MR antagonist or with an aldosterone synthase inhibitor, refers to a patient, or group of patients, who shows or will show a clinically significant relief in the cardiovascular disease when treated with a MR antagonist or with an aldosterone synthase inhibitor, respectively. According to the method of the invention, a patient is classified as a responder to a treatment if the expression of one or two biomarkers selected from the group consisting of the Neutrophil Gelatinase-Associated Lipocalin (NGAL) gene and the SERPINA3 gene, in said patient is significantly different from the predetermined value obtained from the general population or from healthy subjects. Preferably, a patient is a responder if the expression level of one or two biomarkers selected from the group consisting of the Neutrophil Gelatinase-Associated Lipocalin (NGAL) gene and the SERPINA3 gene, in said patient is higher than the predetermined value obtained from the general population or from healthy subjects.

Typically, the expression level of said one or two biomarkers in a patient is deemed to be higher than the predetermined value obtained from the general population or from healthy subjects if the ratio of the expression level of said one or two biomarkers in said patient to that of said predetermined value is higher than 1.2, preferably 1.5, even more preferably 2, even more preferably 5, 10 or 20.

The term "healthy subjects" as used herein refers to a population of subjects who do not suffer from any known condition, and in particular, who are not affected with any cardiovascular disease, diabetes, obesity, or metabolic syndrome.

The term "biological sample" means any biological sample derived from a patient. Examples of such samples include fluids, tissues, cell samples, organs, biopsies, etc. Preferred biological samples are a cell or tissue sample. Preferred biological samples are whole blood, serum, plasma or urine.

The term "biomarker", as used herein, refers generally to a molecule, i.e., a gene (or nucleic acid encoding said gene), protein, the expression of which in a biological sample from a patient can be detected by standard methods in the art (as well as those disclosed herein), and is predictive or denotes a condition of the patient from which it was obtained.

Predictive Methods of the Invention

The present invention relates to a method for assessing the MR activation in a patient comprising determining in a biological sample obtained from said patient the expression level of one or two biomarkers selected from the group consisting of the Neutrophil Gelatinase-Associated Lipocalin (NGAL) gene and the SERPINA3 gene.

In a particular embodiment, the invention relates to a method for assessing the MR activation in the cardiovascular system of said patient comprising determining in a biological sample obtained from said patient the expression level of one or two biomarkers selected from the group consisting of the Neutrophil Gelatinase-Associated Lipocalin (NGAL) gene and the SERPINA3 gene.

The present invention also relates to a method for predicting the responsiveness of a patient to a treatment with a MR antagonist or an aldosterone synthase inhibitor, said method comprising determining in a biological sample obtained from said patient the expression level of one or two biomarkers selected from the group consisting of the Neutrophil Gelatinase-Associated Lipocalin (NGAL) gene and the SERPINA3 gene.

In a particular embodiment, the patient is affected with a cardiovascular disease. More particularly, said patient is affected with endothelial dysfunction, coronary artery disease, angina pectoris, myocardial infarction, congestive heart failure, hypertension, cerebrovascular disease, stroke, transient ischemic attacks, deep vein thrombosis, peripheral artery disease, cardiomyopathy, arrhythmias, aortic stenosis, or aneurysm. In a particular embodiment, said patient is affected with congestive heart failure or hypertension.

In a particular embodiment, the patient with a cardiovascular disease has already been treated with a standard treatment selected in the group consisting of angiotensin-converting enzyme inhibitor, diuretics, vasodilators, beta-blockers, *digitalis*, and anticoagulants.

In another particular embodiment, the patient is affected with obesity, diabetes or metabolic syndrome. Actually, it has been shown that MR activation was associated with the pathophysiological development of obesity and metabolic syndrome (Caprio M. et al. 2007; Lamounier-Zepter V. et al. 2005).

In one embodiment, the invention relates to a method for assessing the MR activation in a patient comprising determining the quantity of the one or two biomarkers mRNA in a cell or tissue sample obtained from said patient.

The present invention also relates to a method for predicting the responsiveness of a patient to a treatment with a MR antagonist or an aldosterone synthase inhibitor, said method comprising determining the quantity of the one or two biomarkers mRNA in a cell or tissue sample obtained from said patient.

Peripheral blood mononuclear cells (PBMCs), macrophages, polynuclear cells, and endothelial cells and endothelial promoter cells (EPCs) are the preferred cells. Even more preferably, the cells according to the invention are PBMCs or endothelial cells. Total RNAs can be easily extracted therefrom. The cell or tissue sample may be treated prior to its use, e.g. in order to render nucleic acids available. Techniques of cell or protein lysis, concentration or dilution of nucleic acids, are known by the skilled person.

Determination of the expression level of a gene can be performed by a variety of techniques. Generally, the expression level as determined is a relative expression level.

More preferably, the determination comprises contacting the sample with selective reagents such as probes, primers or ligands, and thereby detecting the presence, or measuring the amount of nucleic acids of interest originally in the sample.

In a preferred embodiment, the expression level may be determined by determining the quantity of mRNA.

Methods for determining the quantity of mRNA are well known in the art. For example the nucleic acid contained in the samples (e.g., cell or tissue prepared from the patient) is first extracted according to standard methods, for example using lytic enzymes or chemical solutions or extracted by nucleic-acid-binding resins following the manufacturer's instructions. The extracted mRNA is then detected by hybridization (e. g., Northern blot analysis) and/or amplification (e.g., RT-PCR). In a preferred embodiment, the expression level of the one or two biomarkers is determined by RT-PCR, preferably quantitative or semi-quantitative RT-PCR, even more preferably real-time quantitative or semi-quantitative RT-PCR. In a preferred embodiment, the expression level of the NGAL gene is assessed by quantitative PCR using forward 5'-GGACCAGGGCTGTCGCTACT-3' (SEQ ID NO:1) and Reverse 5'-GGTGGCCACTTGCACATTGT-3' (SEQ ID NO:2) primers, or forward 5'-TCACCCTGTACGGAAGAACC-3' (SEQ ID NO:3) and reverse 5'-GGTGGGAACAGAGAAAACGA-3' (SEQ ID NO:4) primers.

Other methods of amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e. g. avidin/biotin).

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In another embodiment, the invention relates to a method for assessing the MR activation of a patient comprising measuring the concentration of the one or two biomarkers proteins in a biological sample obtained from said patient.

In another embodiment, the invention relates to a method for predicting the responsiveness of a patient to a treatment with a MR antagonist or an aldosterone synthase inhibitor comprising measuring the concentration of the one or two biomarkers proteins in a biological sample obtained from said patient.

In a preferred embodiment, the concentration of the one or two biomarkers protein is measured in a blood sample, a plasma sample, a serum sample or a urine sample obtained from said patient.

In a particular embodiment, the methods of the invention comprise contacting the biological sample with a binding partner capable of selectively interacting with the one or two biomarkers proteins present in the biological sample. The binding partner may be an antibody that may be polyclonal or monoclonal, preferably monoclonal. In another embodiment, the binding partner may be an aptamer.

Polyclonal antibodies of the invention or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred.

Monoclonal antibodies of the invention or a fragment thereof can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985).

Alternatively, techniques described for the production of single chain antibodies (see e.g. U.S. Pat. No. 4,946,778) can be adapted to produce anti-NGAL or anti SERPINA3, single chain antibodies. Antibodies useful in practicing the present invention also include anti-NGAL or anti SERPINA3 fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to NGAL or to SERPINA3. For example, phage display of antibodies may be used. In such a method, single-chain Fv (scFv) or Fab fragments are expressed on the surface of a suitable bacteriophage, e. g., M13. Briefly, spleen cells of a suitable host, e. g., mouse, that has been immunized with a protein are removed. The coding regions of the VL and VH chains are obtained from those cells that are producing the desired antibody against the protein. These coding regions are then fused to a terminus of a phage sequence. Once the phage is inserted into a suitable carrier, e. g., bacteria, the phage displays the antibody fragment. Phage display of antibodies may also be provided by combinatorial methods known to those skilled in the art. Antibody fragments displayed by a phage may then be used as part of an immunoassay.

Monoclonal antibodies for NGAL are described, for example, in Kjeldsen et al., (1996). Examples of commercially available monoclonal antibodies for NGAL include those obtained from the Antibody Shop, Copenhagen, Denmark, as HYB-211-01, HYB-211-02, and NYB-211-05. Typically, HYB-211-01 and HYB-211-02 can be used with NGAL in both its reduced and unreduced forms. NGAL antibodies can also be purchased from R&D Systems under reference AF1857.

Examples of commercially available monoclonal antibodies for SERPINA3 include those obtained from Abgent, Inc. San Diego and from Sigma-Aldrich Co.

In another embodiment, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. 1997. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consist of conformationally constrained antibody variable regions displayed by a platform protein, such as *E. coli* Thioredoxin A, that are selected from combinatorial libraries by two hybrid methods (Colas et al., 1996).

The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal.

As used herein, the term “labelled”, with regard to the antibody, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be labelled with a radioactive molecule by any method known in the art. For example radioactive molecules include but are not limited radioactive atom for scintigraphic studies such as I123, I124, In111, Re186, Re188.

The aforementioned assays generally involve the binding of the binding partner (i.e. Antibody or aptamer) to a solid support. Solid supports which can be used in the practice of the invention include substrates such as nitrocellulose (e. g., in membrane or microtiter well form); polyvinylchloride (e. g., sheets or microtiter wells); polystyrene latex (e.g., beads or microtiter plates); polyvinylidine fluoride; diazotized paper; nylon membranes; activated beads, magnetically responsive beads, and the like.

The concentration of one or two biomarkers proteins may be measured by using standard immunodiagnostic techniques, including immunoassays such as competition, direct reaction, or sandwich type assays. Such assays include, but are not limited to, agglutination tests; enzyme-labelled and mediated immunoassays, such as ELISAs; biotin/avidin type assays; radioimmunoassays; immunoelectrophoresis; immunoprecipitation.

More particularly, an ELISA method can be used, wherein the wells of a microtiter plate are coated with a set of antibodies which recognize said one or two biomarkers proteins. A biological sample containing or suspected of containing said one or two biomarkers proteins is then added to the coated wells. After a period of incubation sufficient to allow the formation of antibody-antigen complexes, the plate(s) can be washed to remove unbound moieties and a detectably labelled secondary binding molecule added. The secondary binding molecule is allowed to react with any captured sample marker protein, the plate washed and the presence of the secondary binding molecule detected using methods well known in the art.

Suitable ELISA methods for the detection of NGAL were described in Kjeldsen et al. (1996), Mishra J. et al. (2005) and Wang et al. (2007). A sandwich enzyme immunoassay for the detection of NGAL was described by Blaser J. et al. (1995). A radioimmunoassay for the detection of NGAL was described by Xu S Y. et al. (1994).

ELISA kits for detecting NGAL are commercially available from AntibodyShop (Grusbakken 8 DK-2820 Gentofte—Denmark) under the reference KIT 036 or KIT 037, from R&D Systems Europe (Lille—France) under the reference DLCN20 and from MBL International, Woburn, Mass. 01801, USA) under reference CY-8070. An immunoassay for quantifying NGAL/MMP9 complex concentrations is commercially available from R&D Systems Europe (Lille—France) under the reference DM9L20.

Measuring the concentration of the one or two biomarkers proteins (with or without immunoassay-based methods) may also include separation of the compounds: centrifugation based on the compound’s molecular weight; electrophoresis based on mass and charge; HPLC based on hydrophobicity; size exclusion chromatography based on size; and solid-phase affinity based on the compound’s affinity for the particular solid-phase that is used. Once separated, said one or two biomarkers proteins may be identified based on the known “separation profile” e. g., retention time, for that compound and measured using standard techniques.

Alternatively, the separated compounds may be detected and measured by, for example, a mass spectrometer.

In one embodiment, the method of the invention further may comprise a step of comparing the concentration of said one or two biomarkers proteins with a predetermined threshold value. Said comparison is indicative of the MR activation in the patient or the responsiveness of the patient to the treatment with a MR antagonist. Typically, a human patient can be deemed to be a responder to treatment if the concentration of the blood NGAL protein prior to treatment is higher than 70 μg/l, preferably higher than 80 μg/l, even more preferably higher than 85 μg/l 90 μg/l, 95 μg/l, 100 μg/l, 125 μg/l, 150 μg/l or 200 μg/l.

Kits of the Invention

A further embodiment of the invention provides kits comprising materials useful for carrying out the method for assessing the MR activation in a patient and the method for predicting the responsiveness of a patient to a treatment with a MR antagonist or an aldosterone synthase inhibitor. These methods may be performed by diagnostics laboratories, experimental laboratories or practitioners. The invention provides kits that can be used in these different settings.

Material and reagents for detecting NGAL and/or SERPINA3 in a biological sample may be assembled together in a kit.

An embodiment of the invention relates to a kit comprising:

a) means for detecting the NGAL protein; and b) means for detecting the SERPINA3 protein.

Typically said kit comprises:

a) a binding partner of the NGAL protein; and b) a binding partner of the SERPINA3 protein.

Typically said binding partner is an antibody.

The binding partner can be tagged for an easier detection. It may or may not be immobilized on a substrate surface (e.g., beads, array, and the like). Typically, a substrate surface (e.g. membrane) may be included in the kit for immobilization of the binding partner (e.g., via gel electrophoresis and transfer to membrane).

In addition, a kit of the invention generally also comprises at least one reagent for the detection of a complex between binding partner included in the kit and biomarker of the invention.

Depending on the procedure, the kit may further comprise one or more of: extraction buffer and/or reagents, western blotting buffer and/or reagents, and detection means. Protocols for using these buffers and reagents for performing different steps of the procedure may be included in the kit.

The different reagents included in a kit of the invention may be supplied in a solid (e.g. lyophilized) or liquid form. The kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale.

In certain embodiments, a kit comprises instructions for using its components for the prediction of a heart failure risk in a subject according to a method of the invention. Instructions for using the kit according to methods of the invention may comprise instructions for processing the biological sample obtained from the subject and/or for performing the test, or instructions for interpreting the results. A kit may also contain a notice in the form prescribed by a governmental agency regulating the manufacture, use or sale of pharmaceuticals or biological products.

Therapeutic Methods of the Invention

The method of the invention may be useful for classifying patients affected by cardiovascular disease and then may be used to choose the accurate treatment for said patient. For example, patients classified as responder or non responder may thus receive an appropriate amount of the MR antagonist or aldosterone synthase inhibitor. Such a method may thus help the physician to make a choice on a therapeutic treatment. Costs of the treatments may therefore be adapted to risk of the patients.

Thus another aspect of the invention relates to a method for treating a patient affected with and/or preventing in a patient at risk of a disease comprising the steps consisting in:

a) determining whether said patient is a responder or a non responder to a treatment with a MR antagonist or an aldosterone synthase inhibitor, by performing the in vitro method for predicting the responsiveness of said patient according to the invention, wherein the patient is classified as a responder if the expression level of said one or two biomarkers in said patient is higher than the predetermined value obtained from the general population or from healthy subjects and b) administering a MR antagonist or an aldosterone synthase inhibitor to said patient, if said patient has been determined as a responder at step a).

In a preferred embodiment, said disease is a cardiovascular disease.

In another embodiment, said disease is metabolic syndrome, obesity or diabetes.

The MR antagonist or aldosterone synthase inhibitor may be administered in the form of a pharmaceutical composition. Preferably, said antagonist or inhibitor is administered in a therapeutically effective amount.

By a “therapeutically effective amount” is meant a sufficient amount of the MR antagonist or inhibitor to treat and/or to prevent cardiovascular disease at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

A further object of the invention is the use of a MR antagonist or an aldosterone synthase inhibitor, for the preparation of a medicament for treating a patient affected with a cardiovascular disease, diabetes, obesity or metabolic syndrome, said patient being classified as responder by the method as above described.

A further object of the invention relates to a MR antagonist or an aldosterone synthase inhibitor for treating a patient affected with a cardiovascular disease, diabetes, obesity or metabolic syndrome, said patient being classified as responder by the method of the invention.

A further object of the invention thus relates to a MR antagonist or an aldosterone synthase inhibitor for treating a patient affected with a cardiovascular disease, diabetes, obesity or metabolic syndrome, wherein said patient has an expression level of said one or two biomarkers higher than a predetermined value obtained from the general population or from healthy subjects.

In a preferred embodiment, said patient is affected with a cardiovascular disease.

In a preferred embodiment, said patient is affected with obesity.

In a preferred embodiment, said patient is affected with diabetes.

In a preferred embodiment, said patient is affected with metabolic syndrome.

Another object of the invention is the use of one or two biomarkers selected from the group consisting of the Neutrophil Gelatinase-Associated Lipocalin (NGAL) gene and the SERPINA3 gene, as biomarker(s) of MR activation in a patient.

Another object of the invention is a method for monitoring a treatment of a patient with a MR antagonist or an aldosterone synthase inhibitor comprising assessing the MR activation by the method according to the invention, and optionally, comparing the expression level of said one or two biomarkers with a predetermined value representing a predetermined stage of the MR activation, the expression level of said one or two biomarkers with respect to the predetermined value indicating the evolution of the MR activation, and therefore the degree of efficacy of the treatment.

The invention will further be illustrated in view of the figures and examples.

FIGURE LEGENDS

FIG. 1A: Time course of NGAL expression in models with conditional MR cardiac overexpression. Lcn2 stands for lipocalin2 (NGAL). HPRT stands for housekeeping control gene. Cnt stands for control littermate mice. DT stands for double-transgenic mice with conditional hMR overexpression.

Figure 1B:
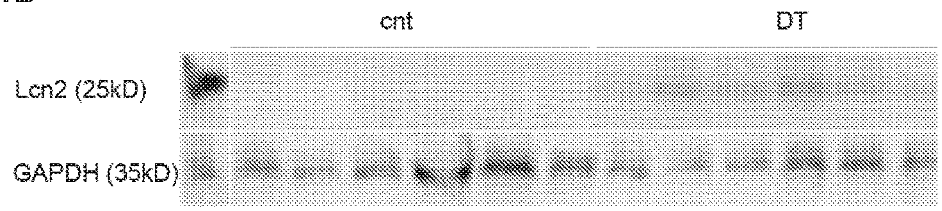

FIG. 1B: NGAL protein expression in the heart of MR. Lcn2 stands for lipocalin2 (NGAL). GAPDH stands for housekeeping control protein. Cnt stands for control littermate mice. DT stands for double-transgenic mice with conditional hMR overexpression.

Figure 2:
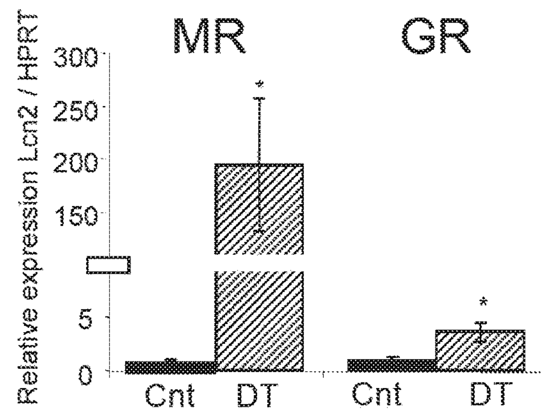

FIG. 2: NGAL expression in the heart of MR versus GR overexpressing mice. Lcn2 stands for lipocalin2 (NGAL). HPRT stands for housekeeping control gene. Cnt stands for control littermate mice. DT stands for double-transgenic mice with conditional hMR or hGR overexpression.

FIG. 3A-3D: NGAL expression in various models. FIG. 3A and FIG. 3B: quantitative PCR; FIG. 3C and FIG. 3D: ELISA. Cnt stands for control littermate mice. DT stands for double-transgenic mice with conditional hMR overexpression. Aldo-salt means uninephrectomized mice treated with aldosterone infusion and drinking 1% NaCl. Endothelial-specific MR expression is obtained by conditional MR expression targeted to the endothelium only.

FIG. 4A-4D: Expression of NGAL in a cellular model of rat cardiomyocyte (H9C2 cells) stably expressing rat MR. Cnt stands for control (diluent). Aldo and cortico stand for aldosterone and corticosterone, respectively. RU28318 is an MR antagonist, RU 486 is a GR antagonist. Bactin is a housekeeping gene used for normalization.

Figure 5A:
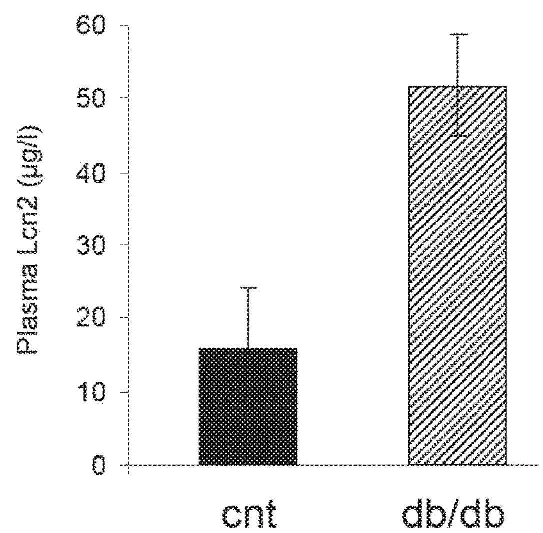

FIG. 5A: Expression of NGAL in a mouse model of type II diabetes. Lcn2 stands for lipocalin2 (NGAL). Cnt stands for control littermate mice. Db/db stands for diabetic mice.

Figure 5B:
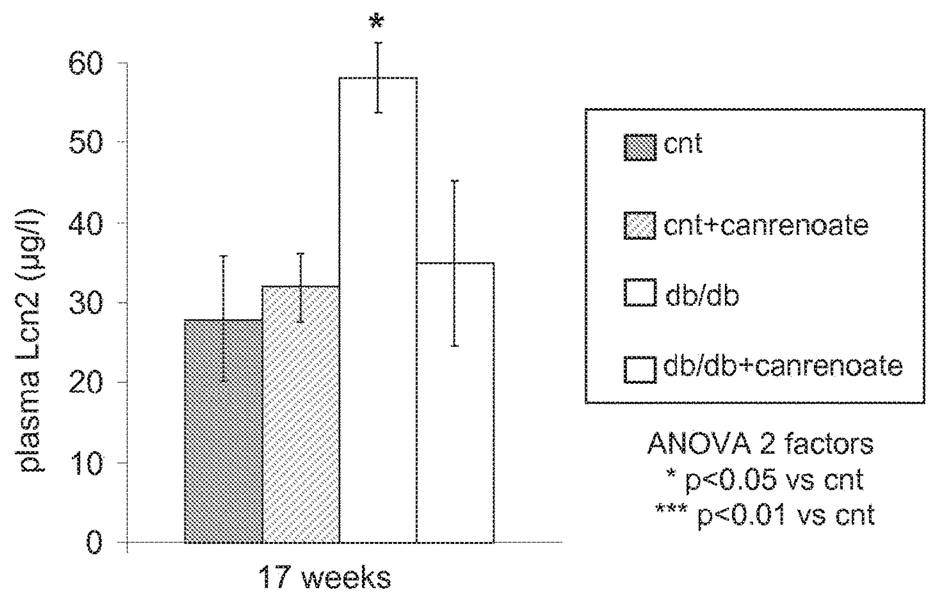

FIG. 5B: Evolution of the lipocalin2/NGAL plasma levels. Plasma lcn2 in control and db/db mice, with or without treatment with canrenoate for 17 weeks.

Figure 6A:
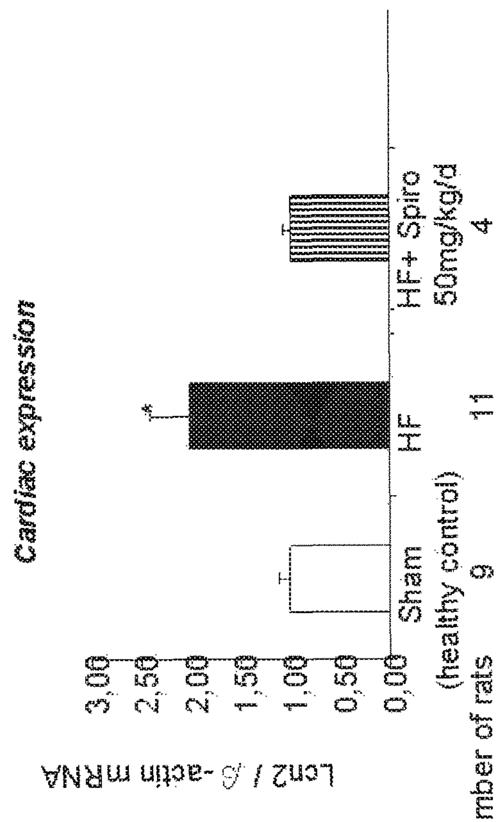
Figure 6B:
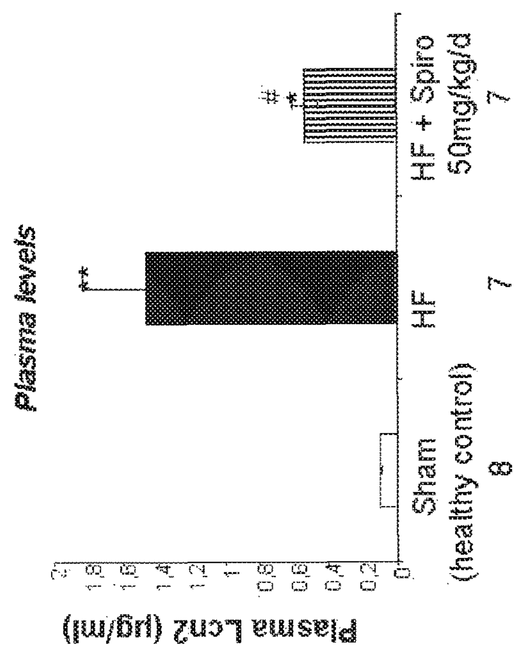

FIG. 6A-6B: MR-dependent induction of lipocalin2/NGAL in the heart and plasma of rats with cardiac failure. FIG. 6A. The expression of lipocalin2/NGAL is increased 2-fold in the cardiac left ventricle of rats with cachexia-induced heart failure. Induction is fully prevented by effective dose of spironolactone (50 mg/Kg/day, able to prevent heart failure symptoms). FIG. 6B. Plasma levels of lipocalin2/NGAL are also increased in the plasma of the rat with heart failure (FIG. 6B). The increase is prevented when animals are treated with spiro 50 mg/Kg/j (HF+spiro 50 mg/Kg/j versus HF).

Figure 7:
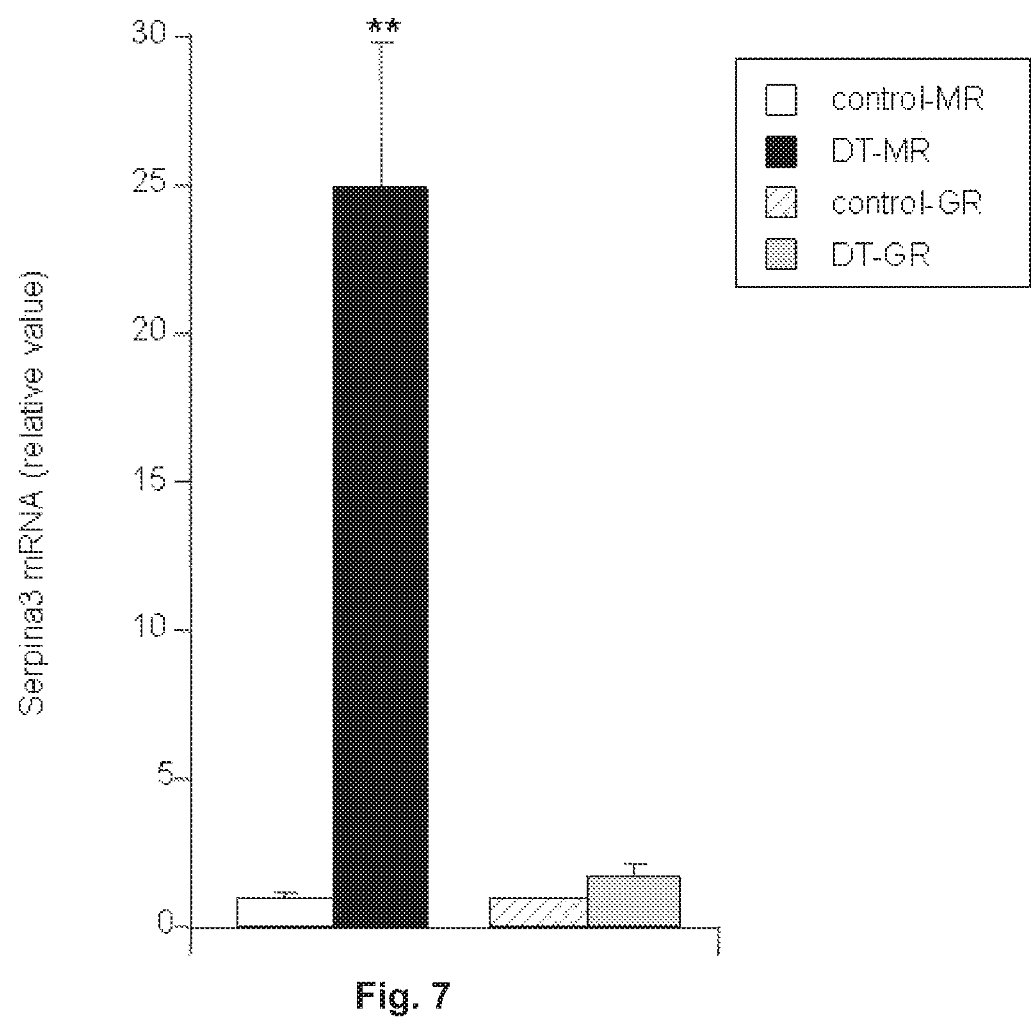

FIG. 7: Validation of differential genes identified in microarray analysis on the mouse model of cardiac overexpression of MR. The expression of Serpina3, is significantly increased in the heart of mice overexpressing the MR (DT-MR), but not modified in the heart of mice overexpressing the GR(DT-GR). Values of mRNA levels were normalized for ubc mRNA levels in each sample. These values in control were set as 1 for each gene, and fold changes are shown on the figure. *, $p<0.05$, **, $p<0.01$ vs control, using Mann-Whitney U test.

Figure 8:
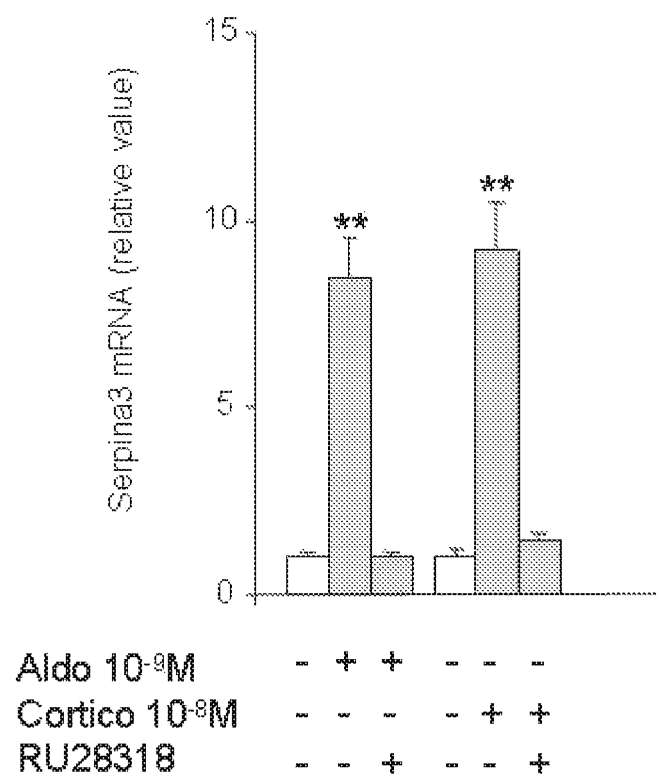

FIG. 8: MR specificity of the Expression of serpina3 in H9C2/MR cells. The expression of serpina3 is increased by 1 nM aldosterone (aldo) and 10 nM corticosterone (cortico) for 24 h, via a MR-dependant mechanism as shown using the RU28318, a specific MR antagonist. Values of mRNA levels were normalized for β-actin mRNA levels in each sample. These values in control (nontreated cells) were set as 1 for each gene, and fold changes are shown on the figure. **, $p<0.01$ vs. control (no steroid), using ANOVA analysis.

Figure 9A:
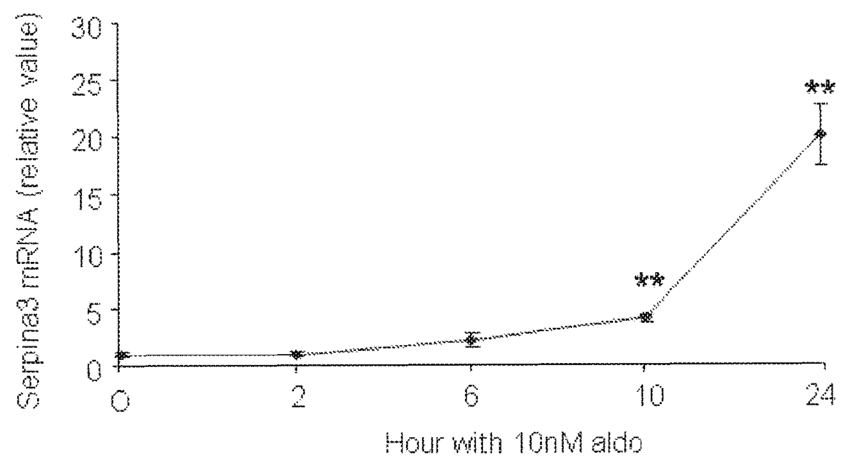

FIG. 9A: time-course of Serpina3 induction in H9C2/MR cells treated with 10 nM aldosterone.

Serpina3 expression is highly induced after 24 h exposure to aldosterone. Values of mRNA levels were normalized for β-actin mRNA levels in each sample. These values in control (nontreated cells) were set as 1 for each gene, and fold changes are shown on the figure. *, $p<0.05$, **, $p<0.01$ vs. control (no steroid), using ANOVA analysis.

Figure 9B:
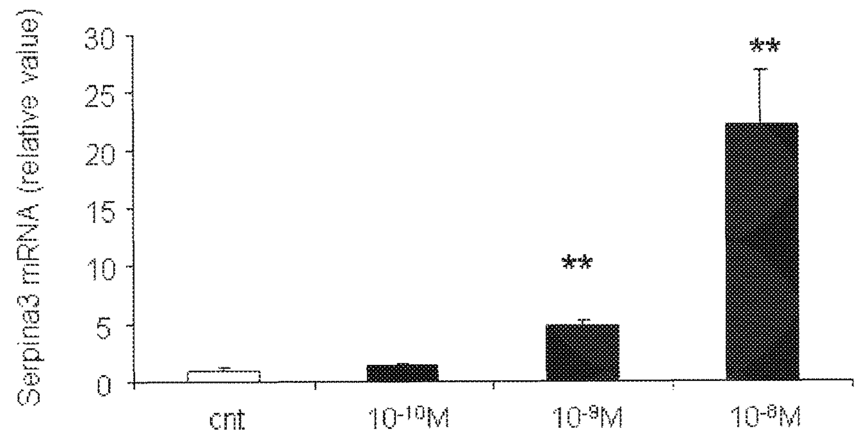

FIG. 9B: Dose-response of Serpina3 induction with aldosterone.

Induction of Serpina3 expression by aldosterone is dose-dependent. Values of mRNA levels were normalized for β-actin mRNA levels in each sample. These values in control (nontreated cells) were set as 1 for each gene, and fold changes are shown on the figure. *, $p<0.05$, **, $p<0.01$ vs. control (no steroid), using ANOVA analysis.

Figure 10:
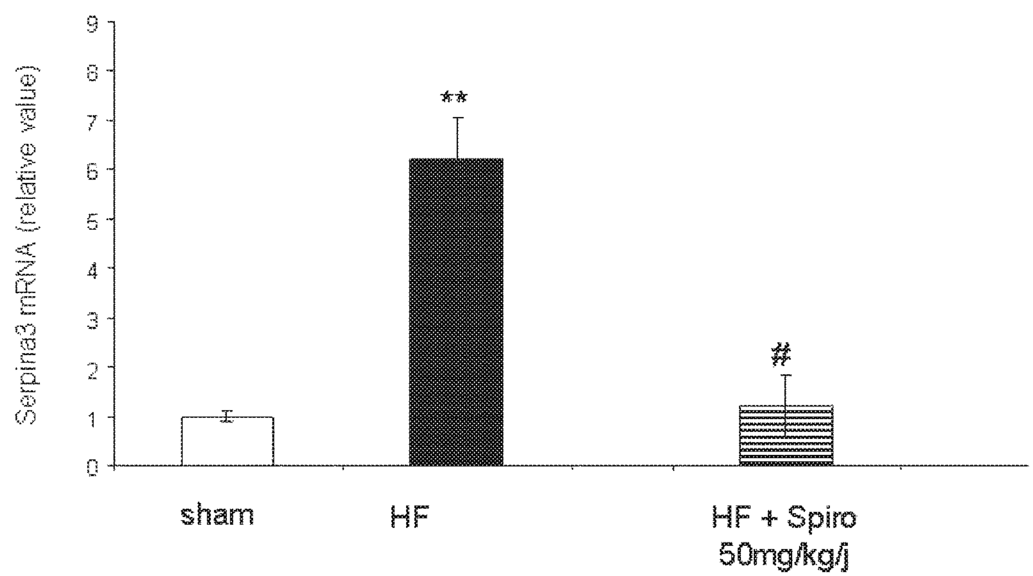

FIG. 10 MR-dependent induction of Serpina3 in the heart of rats with cardiac failure.

The expression of Serpina3 is highly increased in the cardiac left ventricle of rats with cachexia-induced heart failure. Induction is prevented by effective dose of spironolactone (50 mg/Kg/day, able to prevent heart failure symptoms). **, $p<0.01$ vs. sham #, $p<0.05$, vs. Placebo (heart failure, placebo administration) using ANOVA analysis.

EXAMPLE 1

MR and GR Transgenic Mice

Mineralocorticoid receptor (MR) and glucocorticoid receptor (GR) transgenic mice allowed conditional expression of the human MR or GR, respectively. MR and GR transgenic mice were obtained by breeding the in-house generated acceptor mice that allowed conditional, inducible expression of hMR or hGR when crossed with appropriate transactivator mice. These conditional transgenic models have been described in Ouvrard-Pascaud et al. (2005) and Sainte-Marie et al. (2007). To identify genes selectively modulated by MR in the heart, the MR and GR acceptor mice were crossed with the MHC-tTA transactivator mice provided by G. Fishman, Columbia University, NY, USA) (Yu et al. 1996) allowing cardiomyocyte-specific expression of hMR and hGR, respectively. This resulted in 4 fold overexpression of MR or 3 fold increase glucocorticoid binding in the heart of MR or GR conditional mice, respectively, as compared to control littermates. To avoid early embryonic lethality, MR progeny were treated with Dox from gestation until birth, allowing expression to occur only by Day 7 after birth.

Samples, RNA Isolation, Labeling and Hybridization:

Total RNA was isolated from whole hearts from 5 one month old MR transgenic mice, 5 one month old GR transgenic mice using TRIZOL® reagent (Life technologies). Reference samples for the MR transgenic mice consisted of whole heart total RNA extracted from 5 control littermates (same age, same breeding) of the MR transgenic mice. Reference samples for the GR transgenic mice consisted of whole heart total RNA extracted from 5 control littermates (same age, same breeding) of the GR transgenic mice. mRNA was isolated using the Oligotex mRNA kit (Qiagen). RNA and mRNA quality was assessed using an Agilent 2100 bioanalyzer. mRNA from MR transgenic mice was pooled and labelled with Cy5 in three separate reactions. mRNA from the reference for MR transgenic mice was pooled and labeled with Cy3 in three separate reactions. mRNA from GR transgenic mice was combined into three pools that were each labeled with Cy5 in two separate reactions. mRNA from the reference for GR transgenic mice was pooled and labeled with Cy3 in six separate reactions. Cy3- and Cy5-labeled cDNA was prepared using the CyScribe cDNA Post Labeling Kit (Amersham Pharmacia Biotech). Labeling reactions were performed separately for each microarray. Three microarray hybridizations were performed for the MR transgenic mice and six for the GR transgenic mice. The hybridization mixture was pre-incubated with human Cot-I DNA (Gibco-BRL), yeast tRNA and polyA RNA and hybridized to a microarray.

Microarrays:

Microarrays were prepared in-house using 50-mer oligonucleotide probes (MWG Biotech®). The probes were spotted onto epoxy-silane coated glass slides using the Lucidea Array Spotter from Amersham. The 5419 genes that were represented on the microarray had been selected for involvement in cardiovascular and/or skeletal muscle normal and pathological functioning. Selection was based on 1) subtractive hybridization experiments (Steenman et al. 2005), 2) genome-wide microarray hybridizations (Steenman et al. 2003) and 3) literature data. The microarray contained both mouse-specific oligonucleotides and human oligonucleotides with at least 80% homology with the corresponding mouse sequence. Each gene probe was spotted in triplicate.

Raw Data Extraction and Consolidation:

Hybridized arrays were scanned by fluorescence confocal microscopy (Scanarray 4000XL, GSI-Lumonics). Fluorescence signal measurements were obtained separately for each fluorochrome at a 10 μm/pixel resolution. Hybridization and background signal intensities, and quality control parameters were measured using GenePix Pro 5.0 (Axone). A Lowess normalization procedure (Yang et al. 2002) was performed to correct for technical biases. The procedure was applied channel-by-channel as described previously (Workman et al. 2002). For each microarray, Cy3- and Cy5-signal intensities were individually normalized to a prototype defined as the median profile of all Cy3- or Cy5-signal intensities.

Statistical Analysis of the Microarrays:

Significance Analysis of Microarrays (SAM) (Tusher et al. 2001) and Linear Models for MicroArray data (Limma) (Smyth 2004) were used to identify genes with statistically-significant differential expression. One-class analysis was used to identify genes differentially expressed between transgenic and reference mice and two-class analysis was used to identify genes differentially expressed between both transgenic mice models. One-class analysis of MR transgenic mice resulted in the identification of 520 genes that were identified both by SAM (FDR (false discovery rate)=0.05%) and Limma ("FDR"-correction, $p<0.01$). One-class analysis of GR transgenic mice resulted in the identification of 1232 genes that were identified both by SAM (FDR=0.03%) and Limma ("FDR"-correction, $p<0.01$). Two-class analysis resulted in the identification of 529 genes that were identified both by SAM (FDR=0.09%) and Limma ("FDR"-correction, $p<0.01$).

Expression of NGAL in Various Transgenic or Pharmacological Mouse Models with MR Activation:

Quantitative NGAL mRNA expression was analyzed by quantitative PCR (Q-PCR, Light Cycler, Biorad) using forward 5'-GGACCAGGGCTGTCGCTACT-3' (SEQ ID NO:1) and Reverse 5'-GGTGGCCACTTGCACATTGT-3' (SEQ ID NO:2) primers on 25 μl of RT-PCR (using the qPCR Core kit for Sybr Green I from Eurogentec) prepared using 2 μg DNA-free total RNA extracted from the heart of one, two and three mo-old MR transgenic mice and compared to matched littermates, as well as two mo-old GR transgenic mice (and respective control littermates). Protein expression of NGAL was analyzed in cardiac protein extracts from two mo-old MR mice using a specific NGAL antibody (AF1857, R&D Systems). Plasma concentration of NGAL was estimated using a murine NGAL-specific ELISA assay (provided by A. Xu, Hong-Kong) (Wang et al., 2007)

Quantitative NGAL mRNA expression was also analyzed by Q-PCR in the heart of mice with uninephrectomy and treated with aldosterone infusion (60 μg/kg/j, 0.25 μl/h ALZET minipumps) and 1% salt in the drinking water for 3 weeks (as compared to uninephrectomized-only control mice), and in thoracic aorta from 9 months-old mice with conditional overexpression of the human MR in the endothelium only obtained after appropriate breeding of the MR transgenic mice described above with an endothelial-specific transactivator mice (provided by L. E. Benjamine, Harvard, USA) (Sun et al., 2005) that allowed conditional expression of hMR in the endothelium only.

Plasma concentration of NGAL was also estimated in the plasma of 3 mo mice with uninephrectomy and treated with aldosterone infusion (60 μg/kg/j, 0.25 μl/h ALZET minipumps) and 1% salt in the drinking water for 3 weeks (as compared to uninephrectomized-only control mice) as well as in 9-mo old mice with endothelial-specific MR overexpression, as compared to control littermates.

Expression of NGAL in a Cellular Model of Rat Cardiomyocyte (H9C2 Cells) Stably Overexpressing with Rat MR (Fejes-toth, Endocrinology, 2007)

Quantitative NGAL mRNA expression was analyzed by quantitative PCR (Q-PCR, Light Cycler, Biorad) using forward 5'-TCACCCTGTACGGAAGAACC-3' (SEQ ID NO:3) and reverse 5'-GGTGGGAACAGAGAAAACGA-3' (SEQ ID NO:4) primers on 25 μl of RT-PCR (using the qPCR Core kit for Sybr Green I from Eurogentec) prepared using 2 μg DNA-free total RNA extracted from rat H9-C2/MR cells treated with various concentrations of aldosterone or $10^{-8}$M corticosterone or $10^{-6}$ M MR antagonist RU 28318 or GR antagonist RU 486, alone or in combination.

Expression of NGAL in a Mouse Model of Type II Diabetes (Db/Db Mice with a Spontaneous Mutation in the Leptin Receptor Gene)

Plasma concentration of NGAL was estimated using a murine NGAL-specific ELISA assay (provided by A. Xu, Hong-Kong) (Wang et al., 2007) in db/db mice before and after treatment with the pharmacological MR antagonist canrenoate (Canrenoate, Sigma-Alderich, 100 mg/Kg/day in the drinking water, 45 days).

Results:

Lipocalin2/NGAL mRNA is strongly expressed (×60-200) in the heart of mice with conditional human MR overexpression (DT) as compared to control littermates (Cnt) at 1, 1.5 or 3 mo of age (FIG. 1A). Lipocalin2/NGAL protein was also strongly induced in the heart of 1.5 mo-old mice with conditional human MR overexpression (DT) as compared to control littermates (Cnt) (FIG. 1B). This is highly sensitive since induction of lipocalin2/NGAL expression in control littermates never exceeded×1.3. Specificity over the closely related GR was assessed by analyzing lipocalin/NGAL expression in the heart of 2 mo-old GR overexpressing mice (FIG. 2). NGAL expression was 75 fold more induced in the heart of MR-overexpressing mice than in GR-overexpressing mice.

Lipocalin2/NGAL expression is increased in the heart of mice with 3 weeks pharmacological MR stimulation (aldo/salt model) as well as in the aorta of 9 months-old mice with conditional MR overexpression targeted to the endothelium (DT, as compared to littermates, Cnt) (FIG. 3 A-C). Interestingly, plasma levels of lipocalin2/NGAL are also increased in these two mouse models, suggesting secretion from the endothelial wall (FIG. 3 B-D).

Figure 4A:
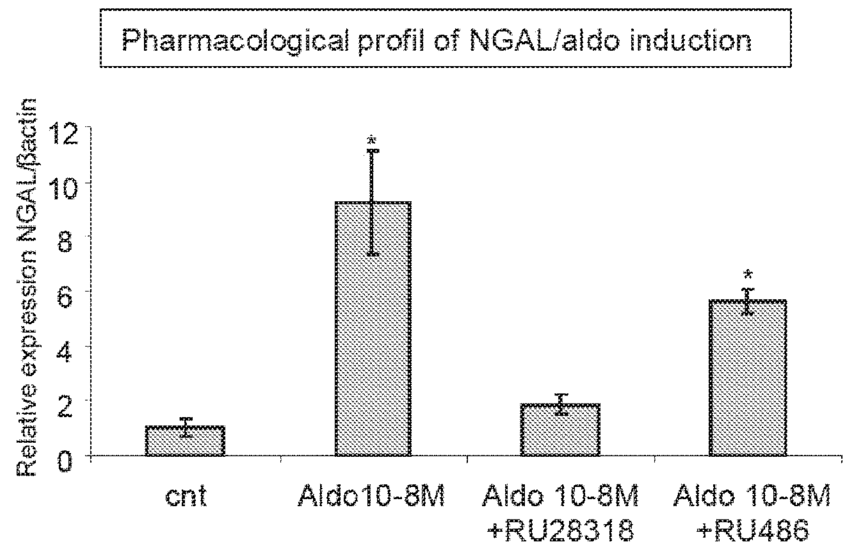
Figure 4B:
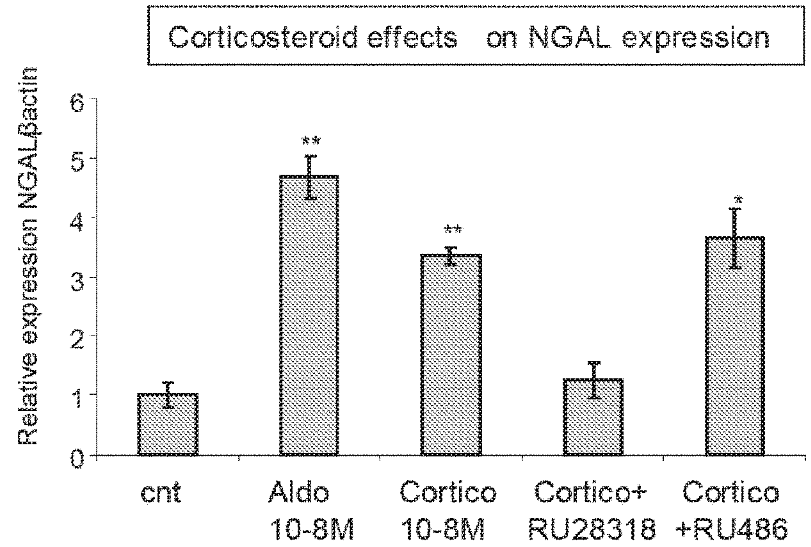
Figure 4C:
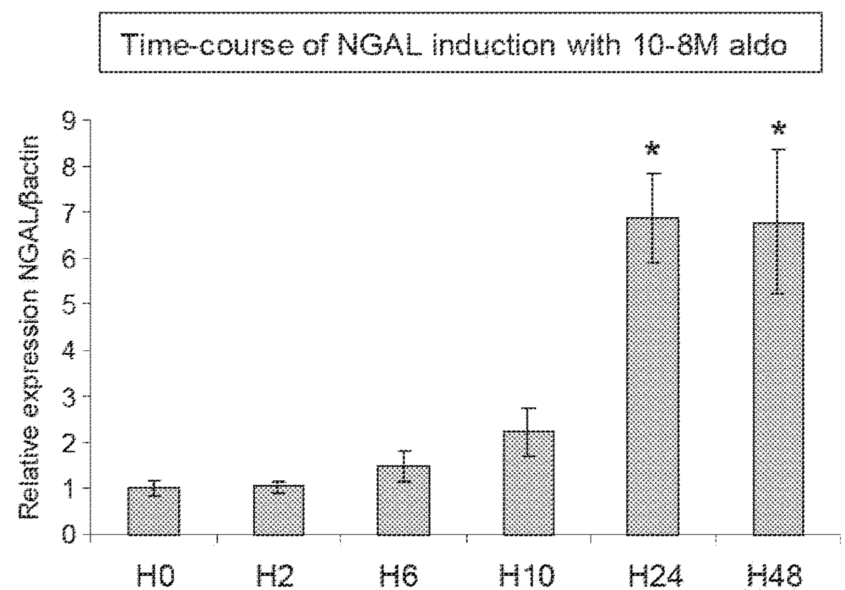
Figure 4D:
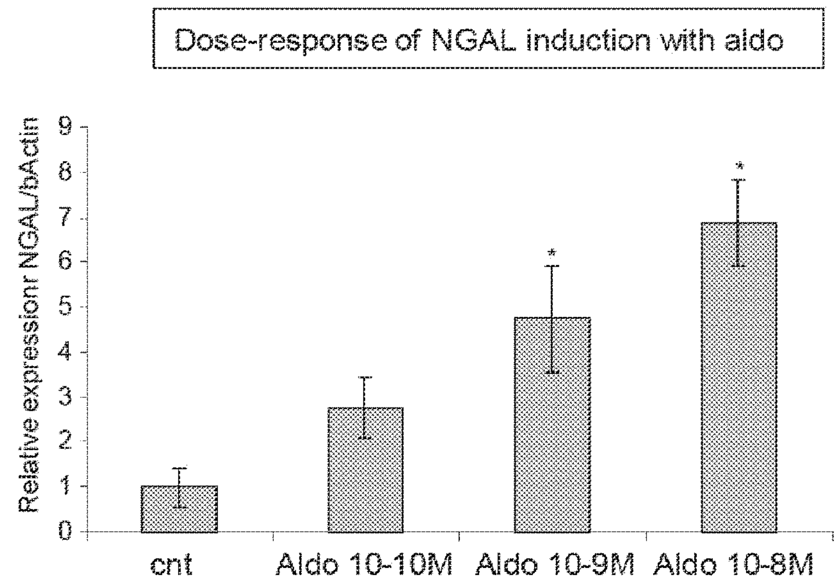

Lipocalin2/NGAL expression is increased in H9C2/MR cells treated with $10^{-8}$M aldosterone for 24 h (FIG. 4A). This increase of Lipocalin2/NGAL expression is prevented by the addition to $10^{-8}$M aldosterone of the MR antagonist RU 28318 but not of the GR antagonist RU 486 (FIG. 4A). $10^{-8}$M Corticosterone (a glucocorticoid hormone) also stimulated Lipocalin2/NGAL expression in H9C2/MR cells (FIG. 4B). This increase is also prevented by the MR antagonist RU 28318 but not by the GR antagonist RU 486 (FIG. 4B), indicating that corticosterone also stimulated Lipocalin2/NGAL expression through the MR. The time-course study indicated that Lipocalin2/NGAL expression was induced after 24 h of $10^{-8}$M aldosterone and remained sustained after 48 h stimulation (FIG. 4C). Lipocalin2/NGAL expression is stimulated by increasing concentrations of aldosterone, indicating a specific MR-mediated effect (FIG. 4D).

Plasma levels of lipocalin2/NGAL are also increased in the plasma of a type II diabetes mouse model (db/db) (FIG. 5A and FIG. 5B control versus db/db). The effect of 17 weeks pharmacological MR antagonism is also analyzed in these mice. FIG. 5B represents the lipocalin2/NGAL plasma levels in control and db/db mice mice, with or without treatment with canrenoate. The increase in plasma levels of lipocalin2/NGAL in db/db mice is prevented by 17 weeks in vivo treatment of the db/db mice with the MR antagonist canrenoate (FIG. 5B, db/db+canrenoate). Canrenoate has no effect on the plasma levels of lipocalin2/NGAL in control mice (control+canrenoate). This demonstrates that plasma level lipocalin2/NGAL can be used to follow efficacy of MR antagonists in type II diabetes.

In a rat model of heart failure (HF) associated to cachexia, cardiac lipocalin2/NGAL mRNA expression, as estimated by real time PCR, is induced up to 2 fold (sham versus MI) (FIG. 6A). When spironolactone is administered to an efficient concentration to prevent the development of heart failure symptom (HF+spiro 50 mg/Kg/j versus HF), induction of lipocalin2/NGAL mRNA is fully prevented (FIG. 6A). Plasma levels of lipocalin2/NGAL are also increased in the plasma of the rat with heart failure (FIG. 6B). The increase is prevented when animals are treated with spiro 50 mg/Kg/j (HF+spiro 50 mg/Kg/j versus HF).

Thus, MR activation can be specifically and efficiently assessed by determining the expression level of the NGAL gene. The responsiveness of a patient to a treatment with a MR antagonist or an aldosterone synthase inhibitor can be predicted by determining the expression level of the NGAL gene in a biological sample obtained from said patient.

EXAMPLE 2

The plasma level of Lcn2/NGAL has been measured in a population of healthy subjects.

Men and women aged between 18 and 85 years-old were included in the study, provided that they had presented no acute pathology in the past 7 days and were not under any cardiovascular treatment. Further exclusion criteria for healthy controls were: known high blood pressure (greater than 140/90 mmHg or greater than 160 mm Hg if older than 65); known renal failure, known diabetes, pregnancy, cancer diagnosed within the past 5 years or evolutive neoplasia, chronic liver pathology, connectivitis, Crohn's disease, evolutive tuberculosis, exertional angina, acute coronarien syndrome, history of coronopathy, carotidien endarterectomy and known abdominal aortic aneurysm.

The plasma level of Lcn2/NGAL of the healthy subjects was generally comprised between 40 and 80 μg/ml.

The plasma level of Lcn2/NGAL of patients affected with a cardiovascular disease, diabetes, obesity or metabolic syndrome is also measured. It is higher than that of the healthy subjects.

EXAMPLE 3

Chronic overexpression of MR or GR in cardiomyocytes may lead to altered signaling pathways, representing adaptations of the cells, different from those induced by short-term corticosteroid treatment. To analyze the molecular consequences of chronic MR activation in vivo in the heart, we investigated cardiac gene expression of MR-cardiac mice using Cardiochips®, i.e. microarrays including 5419 genes that had been selected for their involvement in cardiovascular and/or skeletal muscle normal and pathological functioning. Cardiomyocyte MR overexpression for 6 weeks resulted in about 24 up-regulated and 23 down-regulated genes. Interestingly, most of them differed from GR-regulated genes that were determined in parallel in GR-cardiac mice (about 74 GR up-regulated genes and 70 GR down-regulated genes). Moreover, most of the MR-regulated genes did not change in the GR-cardiac mouse model, indicating that each steroid receptor controls a distinct pattern of gene expression in cardiomyocytes.

MR and GR Transgenic Mice:

Mineralocorticoid receptor (MR) and glucocorticoid receptor (GR) transgenic mice allowed conditional expression of the human MR or GR, respectively. MR and GR transgenic mice were obtained by breeding the in-house generated acceptor mice that allowed conditional, inducible expression of hMR or hGR when crossed with appropriate transactivator mice. These conditional transgenic models have been described in Ouvrard-Pascaud et al. (2005) and Sainte-Marie et al. (2007). To identify genes selectively modulated by MR in the heart, the MR and GR acceptor mice were crossed with the MHC-tTA transactivator mice provided by G. Fishman, Columbia University, NY, USA) (Yu et al. 1996) allowing cardiomyocyte-specific expression of hMR and hGR, respectively. This resulted in 4 fold overexpression of MR or 3 fold increase glucocorticoid binding in the heart of MR or GR conditional mice, respectively, as compared to control littermates. To avoid early embryonic lethality, MR progeny were treated with Dox from gestation until birth, allowing expression to occur only by Day 7 after birth.

Samples, RNA Isolation, Labeling and Hybridization:

Total RNA was isolated from whole hearts from 5 one month old MR transgenic mice, 5 one month old GR transgenic mice using TRIZOL® reagent (Life technologies). Reference samples for the MR transgenic mice consisted of whole heart total RNA extracted from 5 control littermates (same age, same breeding) of the MR transgenic mice. Reference samples for the GR transgenic mice consisted of whole heart total RNA extracted from 5 control littermates (same age, same breeding) of the GR transgenic mice. mRNA was isolated using the Oligotex mRNA kit (Qiagen). RNA and mRNA quality was assessed using an Agilent 2100 bioanalyzer. mRNA from MR transgenic mice was pooled and labelled with Cy5 in three separate reactions. mRNA from the reference for MR transgenic mice was pooled and labeled with Cy3 in three separate reactions. mRNA from GR transgenic mice was combined into three pools that were each labeled with Cy5 in two separate reactions. mRNA from the reference for GR transgenic mice was pooled and labeled with Cy3 in six separate reactions. Cy3- and Cy5-labeled cDNA was prepared using the CyScribe cDNA Post Labeling Kit (Amersham Pharmacia Biotech). Labeling reactions were performed separately for each microarray. Three microarray hybridizations were performed for the MR transgenic mice and six for the GR transgenic mice. The hybridization mixture was pre-incubated with human Cot-I DNA (Gibco-BRL), yeast tRNA and polyA RNA and hybridized to a microarray.

Microarrays:

Microarrays were prepared in-house using 50-mer oligonucleotide probes (MWG Biotech®). The probes were spotted onto epoxy-silane coated glass slides using the Lucidea Array Spotter from Amersham. The 5419 genes that were represented on the microarray had been selected for involvement in cardiovascular and/or skeletal muscle normal and pathological functioning. Selection was based on 1) subtractive hybridization experiments (Steenman et al. 2005), 2) genome-wide microarray hybridizations (Steenman et al. 2003) and 3) literature data. The microarray contained both mouse-specific oligonucleotides and human oligonucleotides with at least 80% homology with the corresponding mouse sequence. Each gene probe was spotted in triplicate.

Raw Data Extraction and Consolidation:

Hybridized arrays were scanned by fluorescence confocal microscopy (Scanarray 4000XL, GSI-Lumonics). Fluorescence signal measurements were obtained separately for each fluorochrome at a 10 μm/pixel resolution. Hybridization and background signal intensities, and quality control parameters were measured using GenePix Pro 5.0 (Axone). A Lowess normalization procedure (Yang et al. 2002) was performed to correct for technical biases. The procedure was applied channel-by-channel as described previously (Workman et al. 2002). For each microarray, Cy3- and Cy5-signal intensities were individually normalized to a prototype defined as the median profile of all Cy3- or Cy5-signal intensities.

Statistical Analysis of the Microarrays:

Significance Analysis of Microarrays (SAM) (Tusher et al. 2001) and Linear Models for MicroArray data (Limma) (Smyth 2004) were used to identify genes with statistically-significant differential expression. One-class analysis was used to identify genes differentially expressed between transgenic and reference mice and two-class analysis was used to identify genes differentially expressed between both transgenic mice models. One-class analysis of MR transgenic mice resulted in the identification of 520 genes that were identified both by SAM (FDR (false discovery rate)=0.05%) and Limma ("FDR"-correction, $p<0.01$). One-class analysis of GR transgenic mice resulted in the identification of 1232 genes that were identified both by SAM (FDR=0.03%) and Limma ("FDR"-correction, $p<0.01$). Two-class analysis resulted in the identification of 529 genes that were identified both by SAM (FDR=0.09%) and Limma ("FDR"-correction, $p<0.01$).

Expression of Serpina3 in Transgenic Mouse Models with MR or GR Activation:

Quantitative Serpina3 mRNA expression was analyzed by quantitative PCR (Q-PCR, Light Cycler, Biorad) using forward 5'-CATCCCTGTGGGAAGTCAGT-3' (SEQ ID NO:5) and Reverse 5'-CTTTTGGGTGGAGGCAGATA-3' (SEQ ID NO:6) primers on 25 μl of RT-PCR (using the qPCR Core kit for Sybr Green I from Eurogentec) prepared using 2 μg DNA-free total RNA extracted from the heart of one, two and three mo-old MR transgenic mice and compared to matched littermates, as well as two mo-old GR transgenic mice (and respective control littermates)

Expression of Serpina3 in a Cellular Model of Rat Cardiomyocyte (H9C2 Cells) Stably Overexpressing with Rat MR (Fejes-toth, Endocrinology, 2007)

Quantitative Serpina3 mRNA expression was analyzed by quantitative PCR (Q-PCR, Light Cycler, Biorad) using forward 5'-AGACAAGGGGACACAACTGG-3' (SEQ ID NO:7) and reverse 5'-TGAGATGCTAAGTGGGGAGAA-3' (SEQ ID NO:8) primers on 25 μl of RT-PCR (using the qPCR Core kit for Sybr Green I from Eurogentec) prepared using 2 μg DNA-free total RNA extracted from rat H9-C2/MR cells treated with various concentrations of aldosterone or $10^{-8}$M corticosterone or $10^{-6}$ M MR antagonist RU 28318, alone or in combination.

Expression of Serpina3 in a Rat Model of Heart Failure Induced by Cachexia. Effect of Pharmacological MR Antagonism with Spironolactone Quantitative Serpina3 mRNA expression was analyzed by quantitative PCR (Q-PCR, Light Cycler, Biorad) using forward 5'-AGACAAGGGGACACAACTGG-3' (SEQ ID NO:7) and reverse 5'-TGAGATGCTAAGTGGGGAGAA-3' (SEQ ID NO:8) primers on 25 μl of RT-PCR (using the qPCR Core kit for Sybr Green I from Eurogentec) prepared using 2 μg DNA-free total RNA extracted from the left ventricles Results:

mRNA expression of the serine-protease inhibitor SERPINA3 (or alpha1-antichymotrypsin), was up-regulated×25 in the heart of MR-cardiac mice, while they did not vary significantly in GR-cardiac mice, as determined by real-time PCR. (FIG. 7)

To investigate possible links between chronic effects of MR and those occurring earlier, some of the in vivo MR-regulated genes identified in the MR-cardiac mice were tested in the H9C2/MR+ cell line. In the presence of low doses of aldosterone (1 nM) for 24 hrs, SERPINA3 mRNA was induced by about 8-fold (FIG. 8). Induction was suppressed in the presence of the MR antagonist RU 28318, demonstrating that it involves specific interactions with the MR. Of note, 10 nM corticosterone has similar effects than aldosterone that were prevented with the MR antagonist (FIG. 8). Time course experiment (FIG. 9A) indicated that serpina3 is induced by Aldosterone 10 nM after 10 hours, with a strong induction (×15) after 24 h. Concentration dependent induction is observed, starting with 1 nM aldosterone (FIG. 9B).

In a rat model of heart failure (HF) associated to cachexia, cardiac Serpina3 mRNA expression, as estimated by real time PCR, is induced up to 6 fold (sham versus HF) (FIG. 10). When spironolactone is administered to an efficient concentration to prevent the development of heart failure symptom (HF+spiro 50 mg/Kg/j versus HF), induction of Serpina3 mRNA is fully prevented (FIG. 10).

These data show that SERPINA3 are involved in the early response to aldosterone in cardiomyocytes, as well as in the chronic adaptation to enhanced MR signaling, as seen in mice overexpressing the MR. Because serpina3 is a secreted enzymes, it can be used as markers of cardiac damage linked to MR activation.

REFERENCES

Throughout this application, various references describe the state of the art to which this invention pertains. The disclosures of these references are hereby incorporated by reference into the present disclosure.

Beato M, Herrlich P, Schutz G. Steroid hormone receptors: many actors in search of a plot. Cell. 1995 Dec. 15; 83(6):851-7.

Blaser J, Triebel S, Tschesche H. A sandwich enzyme immunoassay for the determination of neutrophil lipocalin in body fluids. Clin Chim Acta. 1995; 235(2):137-145.

Bonvalet J P, Alfaidy N, Farman N, Lombes M. Aldosterone: intracellular receptors in human heart. Eur Heart J. 1995 December; 16 Suppl N:92-7.

Brilla C G, Weber K T. Mineralocorticoid excess, dietary sodium, and myocardial fibrosis. J Lab Clin Med. 1992 December; 120(6):893-901.

Caprio M, Feve B, Claes A, Viengchareun S, Lombes M, Zennaro M C. Pivotal role of the mineralocorticoid receptor in corticosteroid-induced adipogenesis. FASEB J. 2007; 21(9):2185-94.

Colas P, Cohen B, Jessen T, Grishina I, McCoy J, Brent R. (1996) Genetic selection of peptide aptamers that recognize and inhibit cyclin-dependent kinase 2. Nature, 380, 548-50.

Cote R J, Morrissey D M, Houghton A N, Beattie E J Jr, Oettgen H F, Old L J. Generation of human monoclonal antibodies reactive with cellular antigens. Proc Natl Acad Sci USA. 1983 April; 80(7):2026-30.

Farquharson C A, Struthers A D. Spironolactone increases nitric oxide bioactivity, improves endothelial vasodilator dysfunction, and suppresses vascular angiotensin 1/angiotensin II conversion in patients with chronic heart failure. Circulation. 2000 Feb. 15; 101(6):594-7.

Fiebeler A, Nussberger J, Shagdarsuren E, Rong S, Hilfenhaus G, Al-Saadi N, Dechend R, Wellner M, Meiners S, Maser-Gluth C, Jeng A Y, Webb R L, Luft F C, Muller D N. Aldosterone synthase inhibitor ameliorates angiotensin II-induced organ damage. Circulation. 2005 Jun. 14; 111(23):3087-94. Epub 2005 Jun. 6.

Funder J W. Glucocorticoid and mineralocorticoid receptors: biology and clinical relevance. Annu Rev Med. 1997; 48:231-40. Review.

Funder J W. Mineralocorticoid receptors and cardiovascular damage: it's not just aldosterone Hypertension. 2006: 47(4):634-5. Review Hatakeyama H, Miyamori I, Fujita T, Takeda Y, Takeda R, Yamamoto H. Vascular aldosterone. Biosynthesis and a link to angiotensin II-induced hypertrophy of vascular smooth muscle cells. J Biol Chem. 1994 Sep. 30; 269 (39):24316-20.

Kjeldsen L, Johnsen A, Sengelov H, Borregaard N. Isolation and primary structure of NGAL, a novel protein associated with human neutrophil gelatinase. J Biol Chem. 1993 May 15; 268(14):10425-32.

Kjeldsen L, Koch C, Arnljots K, Borregaard N. Characterization of two ELISAs for NGAL, a newly described lipocalin in human neutrophils. J Immunol Methods. 1996 Nov. 13; 198(2):155-64.

Kohler G, Milstein C. Continuous cultures of fused cells secreting antibody of predefined specificity. Nature. 1975 Aug. 7; 256(5517):495-7.

Lamounier-Zepter V, Ehrhart-Bornstein M, Bornstein S R. Mineralocorticoid-stimulating activity of adipose tissue. Best Pract Res Clin Endocrinol Metab. 2005 19(4):567-75. Review.

Lombes M, Oblin M E, Gasc J M, Baulieu E E, Farman N, Bonvalet J P. Immunohistochemical and biochemical evidence for a cardiovascular mineralocorticoid receptor. Circ Res. 1992 September; 71(3):503-10.

Mishra J, Dent C, Tarabishi R et al. Neutrophil gelatinase-associated lipocalin (NGAL) as a biomarker for acute renal injury following cardiac surgery. Lancet 2005; 365: 1231-1238.

Nagata K, Obata K, Xu J, Ichihara S, Noda A, Kimata H, Kato T, Izawa H, Murohara T, Yokota M. Mineralocorticoid receptor antagonism attenuates cardiac hypertrophy and failure in low-aldosterone hypertensive rats. Hypertension. 2006 47(4):656-64.

Ouvrard-Pascaud A, Sainte-Marie Y, Benitah J P, Perrier R, Soukaseum C, Cat A N, Royer A, Le Quang K, Charpentier F, Demolombe S, Mechta-Grigoriou F, Beggah A T, Maison-Blanche P, Oblin M E, Delcayre C, Fishman G I, Farman N, Escoubet B, Jaisser F. Conditional mineralocorticoid receptor expression in the heart leads to life-threatening arrhythmias. Circulation. 2005 Jun. 14; 111 (23):3025-33. Epub 2005 Jun. 6.

Pitt B, Remme W, Zannad F, Neaton J, Martinez F, Roniker B, Bittman R, Hurley S, Kleiman J, Gatlin M; Eplerenone Post-Acute Myocardial Infarction Heart Failure Efficacy and Survival Study Investigators. Eplerenone, a selective aldosterone blocker, in patients with left ventricular dysfunction after myocardial infarction. N Engl J Med. 2003 Apr. 3; 348(14):1309-21. Epub 2003 Mar. 31. Erratum in: N Engl J Med. 2003 May 29; 348(22):2271.

Pitt B, Zannad F, Remme W J, Cody R, Castaigne A, Perez A, Palensky J, Wittes J. The effect of spironolactone on morbidity and mortality in patients with severe heart failure. andomized Aldactone Evaluation Study Investigators. N Engl J Med. 1999 Sep. 2; 341(10):709-17.

Sainte-Marie Y, Cat A N, Perrier R, Mangin L, Soukaseum C, Peuchmaur M, Tronche F, Farman N, Escoubet B, Benitah J P, Jaisser F. Conditional glucocorticoid receptor expression in the heart induces atrio-ventricular block. FASEB J. 2007 May 21.

Schepkens H, Vanholder R, Billiouw J M, Lameire N. Life-threatening hyperkalemia during combined therapy with angiotensin-converting enzyme inhibitors and spironolactone: an analysis of 25 cases. Am J Med. 2001 Apr. 15; 110(6):438-41.

Schmidt-Ott K M, Mori K, Li J Y, et al. Dual action of neutrophil gelatinase-associated lipocalin. J Am Soc Nephrol. 2007; 18(2):407-413.

Silvestre J S, Robert V, Heymes C, Aupetit-Faisant B, Mouas C, Moalic J M, Swynghedauw B, Delcayre C. Myocardial production of aldosterone and corticosterone in the rat. Physiological regulation. J Biol Chem. 1998 Feb. 27; 273(9):4883-91.

Smyth G K. Linear models and empirical bayes methods for assessing differential expression in microarray experiments. Statistical Applications in Genetics and Molecular Biology 3[1], Article 3. 2004.

Steenman M, Chen Y-W, Le Cunff M, Lamirault G, Varro A, Hoffman E, Léger J J (2003) Transcriptomal analysis of failing and non-failing human hearts. Physiol Genomics 12:97-112

Steenman M, Lamirault G, Le Meur N, Le Cunff M, Escande D, Léger J J. Distinct molecular portraits of human failing hearts identified by dedicated cDNA microarrays. Eur. J. Heart Fail. 7[2], 157-165. 2005.

Sun J F, Phung T, Shiojima I, Felske T, Upalakalin J N, Feng D, Kornaga T, Dor T, Dvorak A M, Walsh K, Benjamin L E. Microvascular patterning is controlled by fine-tuning the Akt signal. Proc Natl Acad Sci USA. 2005; 102:128-33.

Takeda M, Tatsumi T, Matsunaga S, Hayashi H, Kimata M, Honsho S, Nishikawa S, Mano A, Shiraishi J, Yamada H, Takahashi T, Matoba S, Kobara M, Matsubara H. Spironolactone modulates expressions of cardiac mineralocorticoid receptor and 11 beta-hydroxysteroid dehydrogenase 2 and prevents ventricular remodeling in post-infarct rat hearts. Hypertens Res. 2007 May; 30(5):427-37.

Tanaka J, Fujita H, Matsuda S, Toku K, Sakanaka M, Maeda N. Glucocorticoid- and mineralocorticoid receptors in microglial cells: the two receptors mediate differential effects of corticosteroids. Glia. 1997 May; 20(1):23-37.

Tuerk C., Using the SELEX combinatorial chemistry process to find high affinity nucleic acid ligands to target molecules. Methods Mol Biol. 1997; 67: 219-30.

Tusher V G, Tibshirani R, Chu G (2001) Significance analysis of microarrays applied to the ionizing radiation response. Proc Natl Acad Sci USA 98:5116-5121

Ullian M E, Schelling J R, Linas S L. Aldosterone enhances angiotensin II receptor binding and inositol phosphate responses. Hypertension. 1992 July; 20(1):67-73.

Wang Y, Lam K S, Kraegen E W, Sweeney G, Zhang J, Tso A W, Chow W S, Wat N M, Xu J Y, Hoo R L, Xu A.: Lipocalin-2 is an inflammatory marker closely associated with obesity, insulin resistance, and hyperglycemia in humans. Clinical Chemistry 2007 January; 53(1):34-41.

Workman C, Jensen L J, Jarmer H, Berka R, Gautier L, Nielser H B, Saxild H H, Nielsen C, Brunak S, Knudsen S (2002) A new non-linear normalization method for reducing variability in DNA microarray experiments. Genome Biol 3:research0048

Xu S Y, Petersson C G, Carlson M, et al. The development of an assay for human neutrophil lipocalin (HNL)—to be used as a specific marker of neutrophil activity in vivo and vitro. J Immunol Methods. 1994; 171(2):245-252.

Yang Y H, Dudoit S, Luu P, Lin D M, Peng V, Ngai J, Speed T P (2002) Normalization for cDNA microarray data: a robust composite method addressing single and multiple slide systematic variation. Nucleic Acids Res 30:e15

Young M, Fullerton M, Dilley R, Funder J. Mineralocorticoids, hypertension, and cardiac fibrosis. J Clin Invest. 1994 June; 93(6):2578-83.

Yu Z, Redfern C S, Fishman G I. Conditional transgene expression in the heart. *Circ Res.* 1996; 79:691-697

The invention claimed is:

1. A method for treating a patient affected with a cardiovascular disease, diabetes, obesity or metabolic syndrome, comprising the steps of measuring in a biological sample obtained from said patient an expression level of one or two biomarkers selected from the group consisting of the Neutrophil Gelatinase-Associated Lipocalin (NGAL) gene and the SERPINA3 gene;

comparing said expression level to a reference value determined from corresponding biomarker expression levels obtained from a population of subjects not affected with a cardiovascular disease, diabetes, obesity or metabolic syndrome; and administering to said patient a mineralocorticoid receptor (MR) antagonist or an aldosterone synthase inhibitor if said expression level is higher than the reference value.

2. The method of claim 1, wherein said cardiovascular disease is congestive heart failure or hypertension.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1

ggaccagggc tgtcgctact                                                20


<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2

ggtggccact tgcacattgt                                                20


<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3

tcaccctgta cggaagaacc                                                20


<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4

ggtgggaaca gagaaaacga                                                20


<210> SEQ ID NO 5
```

```
<211> LENGTH: 20
<212> TYPE: DNA
<213> ORGANISM: Artificial
<220> FEATURE:
<223> OTHER INFORMATION: primer

<400> SEQUENCE: 5

catccctgtg ggaagtcagt                                          20


<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6

cttttgggtg gaggcagata                                          20


<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7

agacaagggg acacaactgg                                          20


<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8

tgagatgcta agtggggaga a                                        21
```